United States Patent
Caudle et al.

(10) Patent No.: US 6,816,316 B2
(45) Date of Patent: Nov. 9, 2004

(54) SMOOTHING LASER BEAM INTEGRATION USING OPTICAL ELEMENT MOTION

(75) Inventors: George Caudle, Bonne Terre, MO (US); Herrmann Glockler, Reno, NV (US); Wayne Brewer, Cupertino, CA (US)

(73) Assignee: VISX, Incorporated, Santa Clara, CA (US)

(*) Notice: Subject to any disclaimer, the term of this patent is extended or adjusted under 35 U.S.C. 154(b) by 0 days.

(21) Appl. No.: 10/366,131

(22) Filed: Feb. 12, 2003

(65) Prior Publication Data

US 2004/0042080 A1 Mar. 4, 2004

Related U.S. Application Data

(60) Provisional application No. 60/356,720, filed on Feb. 12, 2002.

(51) Int. Cl.[7] .............................................. G11B 7/135
(52) U.S. Cl. ...................................... 359/637; 359/618
(58) Field of Search ................................ 359/637, 618, 359/634, 635, 636

(56) References Cited

U.S. PATENT DOCUMENTS

| | | | |
|---|---|---|---|
| 3,986,767 A | 10/1976 | Rexer et al. | |
| 4,980,881 A | 12/1990 | Beaujean | |
| 5,365,032 A | 11/1994 | Muller et al. | |
| 5,556,395 A | 9/1996 | Shimmick et al. | |
| 5,620,437 A | 4/1997 | Sumiya | |
| 5,683,379 A | 11/1997 | Hohla | |
| 5,814,042 A | 9/1998 | Zair | |
| 5,825,562 A | 10/1998 | Lai et al. | |
| 5,865,830 A | 2/1999 | Parel et al. | |
| 5,912,775 A | 6/1999 | Glockler | |
| 6,172,329 B1 | 1/2001 | Shoemaker et al. | |
| 6,320,699 B1 | * 11/2001 | Maeda et al. | ............ 359/637 |

* cited by examiner

Primary Examiner—Hung Xuan Dang
(74) Attorney, Agent, or Firm—Townsend & Townsend & Crew LLP; Nathan S. Cassell

(57) ABSTRACT

Embodiments of the present invention provide methods and systems of temporally smoothing the distortion of a light beam caused by imperfections of an optical element or optical system through which the light beam passes. The optical element is moved relative to the light beam to change a position of the imperfections in the path of the light beam to distribute the distortion of the light beam caused by the imperfection without substantially changing the path of the light beam. In some embodiments, the optical element is axially symmetric with respect to its optical axis, and the distortion of the light beam is distributed by rotating the optical element around its optical axis. In some embodiments, the optical element has geometric uniformity relative to a plane or along a line in a plane, and the distortion of the light beam is distributed by moving the optical element along the plane, or along the line of symmetry in the plane.

45 Claims, 9 Drawing Sheets

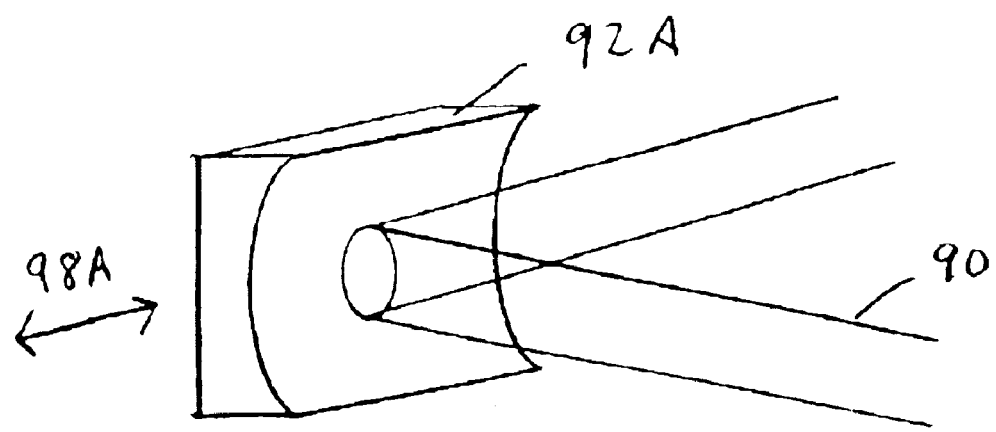
FIG—3B

SMOOTHING LASER BEAM INTEGRATION USING OPTICAL ELEMENT MOTION

CROSS-REFERENCES TO RELATED APPLICATIONS

This application claims benefit to provisional patent application No. 60/356,720, filed on Feb. 12, 2002, the disclosure of which is incorporated herein by reference.

BACKGROUND OF THE INVENTION

The present invention relates generally to systems and methods for modifying the intensity distribution of a light beam, and more particularly to a system and a method for reducing the time average variation in the beam intensity caused by imperfections of an optical element or optical components of the optical system through which the light beam is directed.

Excimer lasers have been used for various applications, including tissue ablation such as corneal ablation and other surgical procedures. The cross-section of the intensity profile of a typical excimer laser beam is typically not spatially uniform. In general, the beam has a generally rectangular cross-section. The intensity along the long axis of the rectangular beam is substantially constant over the central portion of the beam. The intensity along the short axis of the beam is substantially Gaussian. The divergence of the excimer laser beam is different along the two axes. As a result, the beam changes shape as it travels away from the excimer laser.

Producing a laser beam with a substantially uniform intensity is important in many surgical procedures such as tissue ablation, particularly in corneal ablation for refractive correction or therapeutic purposes. In addition, the laser beam should maintain the shape required by the ablation algorithm throughout the ablation procedure.

Various methods have been used to modify the spatial energy intensity distribution of laser beams to generate a beam with more uniform intensity over the beam cross-section at the plane in which the ablation takes place. These methods invariably employ optical elements or systems for focusing, profiling, reflecting, diffracting, imaging, or otherwise optically manipulating the beam. Optical elements are further used to direct the light beam to the desired location such as a surgical site or ablation plane. Examples of optical elements include lenses, mirrors, diffractive optical members, and the like.

Optical elements may have imperfections formed during manufacturing (e.g., scratches, material variations, surface textures, or the like) or caused by artifacts on the surfaces or formed by the interaction of the laser beam with the optical element (compaction, color center formation, or surface degradation). Ultraviolet laser beams cause irregularities in all optics over time. Color centers develop in transparent optics, which then absorb some of the beam. Anti-reflective and high-reflective coatings change or sustain damage. Fused silica transmission optics are compacted in the beam area and change shape. Any imperfection of an optical element, however small, will produce a distortion of a light beam directed through the optical element or reflected by the optical element when the imperfection is disposed in the path of the light beam.

Some optical defects that cause patterns that can be seen in an ablation are very difficult to detect by conventional optical or surface measurements of the optical element. Often, it is very difficult to determine if an optical element has such defects other than by installing the optical element and testing it in a system. This kind of trial testing is time-consuming and can add significant cost to a commercial laser system.

BRIEF SUMMARY OF THE INVENTION

Embodiments of the present invention provide methods and systems for temporally smoothing a distortion of a light beam caused by an imperfection or imperfections of an optical element or optical system in the path of the light beam. The optical element is moved relative to the light beam to change the position of an imperfection in the path of the light beam to spatially distribute over time the distortion of the light beam caused by the imperfections of the optical element. The optical path of the beam is stable so that moving the optical element does not substantially alter the path of the light beam. In addition, moving an optical element to distribute the effect of the imperfections can generally reduce significantly both the rate at which damage occurs to an optical element and the appearance of resulting irregularities in the beam at the final treatment plane.

In accordance with an aspect of the present invention, a method of temporally smoothing a distortion of a light beam includes directing a light beam through an optical system comprising an optical element disposed along a light beam path. The optical element has an imperfection in the path of the light beam causing distortion of an energy profile distribution of the light beam. Moving the optical element with respect to the light beam path changes the position of the imperfection in the path of the light beam, and distributes the distortion caused by the imperfection. The method may include stabilizing the path of the beam as the optical element is moved, and controlling the range of motion of the optical element to be about twice the width of the beam intersecting the element.

In some embodiments, the optical element is axially symmetric with respect to its optical axis, and the distortion introduced into the light beam by the imperfection is distributed by rotating the optical element around its optical axis. The path of the light beam may be parallel or oblique to the axis of symmetry of the optical element. The optical element may be selected from the group consisting of a lens, a mirror, a beam splitter, a transmitting plate, a prism and a diffractive optic.

In some embodiments, the optical element has geometric uniformity relative to a plane, and the distortion of the light beam is distributed by moving the optical element along the plane. The optical element may be moved by translation in at least one direction along the plane. The planar optical element may be moved by rotation around an axis which is perpendicular to the plane. In specific embodiments, the optical element is a planar optical element. The optical element may be selected from the group consisting of a planar mirror, a planar beam splitter, a planar transmitting element, a prism and a planar diffractive optic. In one embodiment, the light beam intersects the optical element over an intersecting surface area of the element, and the range of motion of optical element is less than about 50% of a dimension across the intersecting surface area.

In addition to planar optics such as planar mirrors, planar diffusers, and planar diffractive optics, different optical elements may be used. For instance, other embodiments of the present invention may employ optics which have linear symmetry along a line in a plane, such as cylindrical lenses and mirrors, and linear or cylindrical diffractive optics (e.g., diffractive gratings). For an optical element having geometrical uniformity relative to a line of symmetry in a plane, a driver may oscillate the optical element back and forth along the line of symmetry or move the element slowly in one direction along the line of symmetry and then return it and repeat the motion. The distortion in the light beam is distributed by moving the optical element along the line of symmetry.

In accordance with another aspect of the present invention, a system for temporally smoothing a light beam comprises a light source making a beam of light energy, and an optical element disposed in a path of the light beam. The optical element has an imperfection in the path of the light beam causing a distortion of the energy distribution of the light beam. An optical element driver is coupled with the optical element to move the optical element with respect to the light beam to change a position of the imperfection in the path of the light beam. The change in position of the imperfection distributes the distortion of the light beam caused by the imperfection of the optical element. The path of the light beam may be stable as the driver changes the position of the imperfection. The driver may control a range of motion of the of the optical element to be less than about twice a width of the beam as the beam intersects the element. The light source may be a pulsed laser.

In some embodiments, the optical element has geometric uniformity relative to a plane, and the optical element driver is configured to move the optical element along the plane. In some embodiments, the optical element is axially symmetric with respect to its optical axis, and the optical element driver is configured to rotate the optical element around the optical axis of symmetry thereof. In an embodiment, the light beam intersects the optical element over an intersecting surface area of the element, and the range of motion of the element is less than about 50% of a dimension across the intersecting surface area.

Another aspect of the invention is directed to a method of smoothing an ablation in a material at a treatment plane using a pulsed laser beam. The method comprises making a pulsed laser beam and directing the beam through an optical system comprising an optical element disposed along a laser beam path that directs the laser beam to the treatment plane. The optical element has an imperfection in the path of the laser beam causing distortion of the laser beam. Moving the optical element with respect to the laser beam to changes the position of the imperfection in the path of the laser beam and distributes the distortion caused by the imperfection. The beam ablates the material to form the ablation. The method may include stabilizing the path of the laser beam while moving the optical element. The method may also include controlling a range of motion of the moving element to be less than about twice a width of the beam. The ablation material may be corneal material and the laser may be an excimer laser.

Another aspect of the present invention is directed to a system for forming an ablation at a treatment plane using a pulsed laser beam. The system comprises a pulsed laser source for making a pulsed laser beam. An optical system comprises an optical element disposed along a laser beam path that directs the laser beam to the treatment plane. The optical element has an imperfection in the path of the laser beam causing distortion of the laser beam. An optical element driver coupled with the optical element changes a position of the imperfection in the path of the laser beam and distributes the distortion caused by the imperfection.

BRIEF DESCRIPTION OF THE DRAWINGS

FIG. 3B is a simplified schematic diagram of a cylindrical mirror in accordance with an embodiment of the invention.

DETAILED DESCRIPTION OF THE INVENTION

The present invention is directed to methods and systems of temporally smoothing a distortion in an energy intensity distribution profile of a light beam caused by an imperfection or imperfections of an optical element or optical system in the path of a light beam. As used herein, an imperfection of an optical element or system may encompass an imperfection among many imperfections of the optical element or system. A light beam that passes through an optical system may encompass an optical system having a mirror that reflects a light beam from a surface of the mirror. An illumination surface may encompass an image plane, a laser treatment plane and a theoretical surface where a surface of an object will be positioned to be illuminated. A physical object such as a lens having a uniformity relative to a geometric object such as a line encompasses physical objects for which motion along the geometric object will not substantially deflect a path of a light beam. In other words, the light beam path can be stable with respect to motion of the physical object along the geometric object. In specific embodiments, the invention is applied to an ophthalmological laser surgical optical system.

Figure 1:
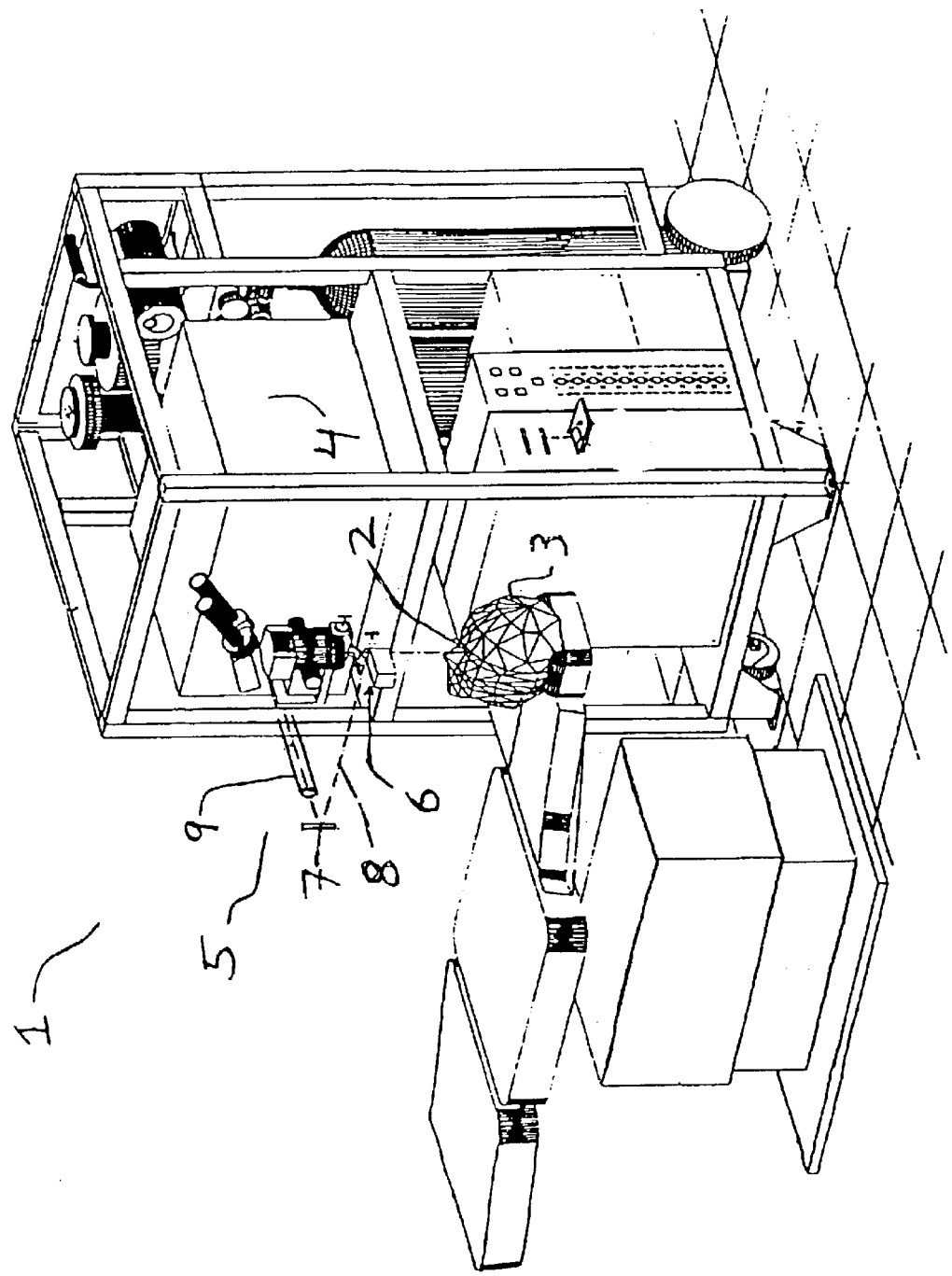
FIG. 1 is a simplified schematic diagram of an embodiment of the invention used to ablate a material such as a cornea of an eye.

An embodiment of an ophthalmic laser surgery system 1 for incorporating the invention and for ablating a material such as a cornea of an eye 2 in a head 3 of a patient is shown in FIG. 1. The system preferably ablates other materials in addition to corneal material. For example, the system 1 may ablate a plastic material during an energy calibration procedure of the system 1. A laser 4 makes a beam 9 of an ablative light energy having an energy intensity profile distribution. The beam 9 of light energy is directed to an optical system 5 that includes a plurality of optical elements such as mirrors 6 and 7. The mirrors 6 and 7 control a path 8 traveled by the beam 9.

Light Beam Integration

FIGS. 1A through 3 illustrate examples of temporally smoothing a distortion to a light beam caused by an imperfection of an optical element by moving the imperfection with respect to the laser beam path. The movements of the optical elements are arranged so that the path of the light beam is substantially unchanged, or stable, as the element moves. The light beam may be generated from any light source and may have any characteristics. For instance, the light beam may be a laser beam generated by an excimer laser.

Figure 1A:
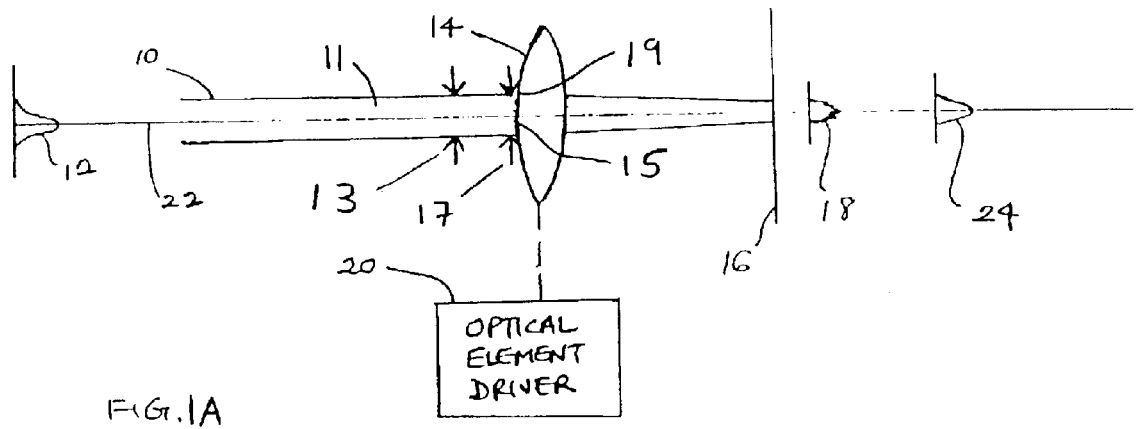
FIG. 1A is a simplified schematic diagram of a light beam passing through a lens with imperfections which is manipulated to reduce the effects of the imperfections of the lens on the light beam by moving the location of the imperfections with respect to the light beam path, in accordance with an embodiment of the present invention.

In FIG. 1A, a light beam 10 has an initial beam energy intensity profile 12. In this embodiment, the profile 12 has a Gaussian distribution. The light beam 10 is directed through a spherical lens 14 onto an illumination surface 16. The light beam 10 travels along a path 11. The light beam 10 has a width 13 as it intersects the optical lens 14. The light beam 10 intersects the lens 14 over an intersecting surface 15 of the lens 14, and the intersecting surface 15 has a dimension 17 across the intersecting surface. The lens 14 has imperfections that may have been formed during manufacturing of the optical material, or may be caused by artifacts on the lens surfaces, or may be caused by interaction of the laser beam with the optical material of the lens 14. The imperfections of the lens 14 which are in the path 11 of the light beam 10 produce distortions of the light beam 10 as it passes through the lens 14, as illustrated in the beam intensity profile 18 at the illumination surface 16. The profile 18 has jagged portions caused by the imperfections.

To reduce the cumulative effects of the imperfections of the lens 14, an optical element driver 20 is provided to move the lens 14 with respect to the light beam 10 so as to change the positions of the imperfections in the path 11 of the light beam 10. As shown in FIG. 1A, the lens 14 has axial symmetry with respect to the optical axis 22 of the lens 14, and the path of the light beam 10 is parallel to the optical axis 22 of the lens 14. In the specific embodiment, the path of the light beam 10 coincides with the optical axis 22 of the lens 14. The optical element driver 20 is configured to rotate the lens 14 around the optical axis 22 so that the imperfections of the lens 14 are moved to various locations in a cross-section of the path 11 of the beam 10 over time. Rotating the lens 14 about the optical axis 22 does not substantially change the path of the beam. Thus, the path of the beam is stable during rotational movement of the lens 14 about optical axis 22. In practice, the tolerances of machined and optical parts may make it difficult to rotate the lens exactly about the optical axis 22. Minor deviations in the position of the optical center 22 about the axis of rotation may occur, and such deviations may induce a slight wobble in the path of the laser beam as the lens rotates. However, these deviations are controlled to be less than about 10% of the diameter of the lens so that a substantial changes in the path of the beam do not occur, and the path of the beam is stable As the beam 10 is projected to the illumination surface 16 for a period of time, the distortion is distributed over different portions of the beam 10 at the illumination surface 16. This movement distributes the distortion caused by the imperfections of the lens 14 in the total energy from the beam incident on a point on the illumination surface 16. The smoothing of the distortion of the beam by distributing the distortion is illustrated in the temporally averaged beam energy intensity profile 24, which is smoother than the profile 18. A peripheral intersecting point 19 is located near the periphery of the intersection of the path 11 of light beam 10 with the lens 14. The peripheral intersecting point 19 rotates about the optical axis 22. The peripheral intersecting point 19 is displaced by a radial distance from the optical axis, and the point travels in an approximately circular trajectory having a circumference and a diameter. A range of motion of the lens encompasses a diameter across an approximately circular trajectory of a peripheral intersecting point 19 as the lens 14 rotates about the optical axis 22. Preferably, a range of motion of the lens 14 is controlled so that the range of motion of the lens 14 is less than about twice a width 13 of the beam 10 as it intersects the lens 14. More preferably, the range of motion of the lens 14 is controlled to be about a dimension 17 across the intersecting surface area 15.

In a specific embodiment, the light beam 10 is a pulsed excimer laser beam generated from a pulsed laser for ablation of an object made of a material such as a corneal material. The spherical lens 14 is located in the path 11 of the beam 10 near an object plane which is imaged near a surface to be ablated from the material. The distortion caused by the imperfections of the lens 14 typically varies the local fluence of the laser beam 10 by a few percent. By rotating the lens 14 relative to the laser beam path 11 during the ablation procedure, the distortion in each laser beam pulse arrives at a different location on the illuminated surface of the ablated material, and the localized effect of the distortion is distributed over the several hundred pulses in a total ablation procedure. A result of the distribution of the distortion to the beam intensity profile is that the distortion in the ablation profile caused by the lens artifacts is greatly reduced and the profile of the ablation in the target material is much smoother.

In other embodiments, the orientation of the path 11 of light beam 10 with respect to the lens 14 may be different from that shown in FIG. 1A. The rotation of the lens 14 can still be employed to distribute the distortion as long as the rotation does not in itself introduce distortion to, or otherwise change the characteristics of, the light beam path 11 (i.e., as long as the refraction of the light beam 10 by the lens 14 along the path 11 remains stable).

Figure 1B:
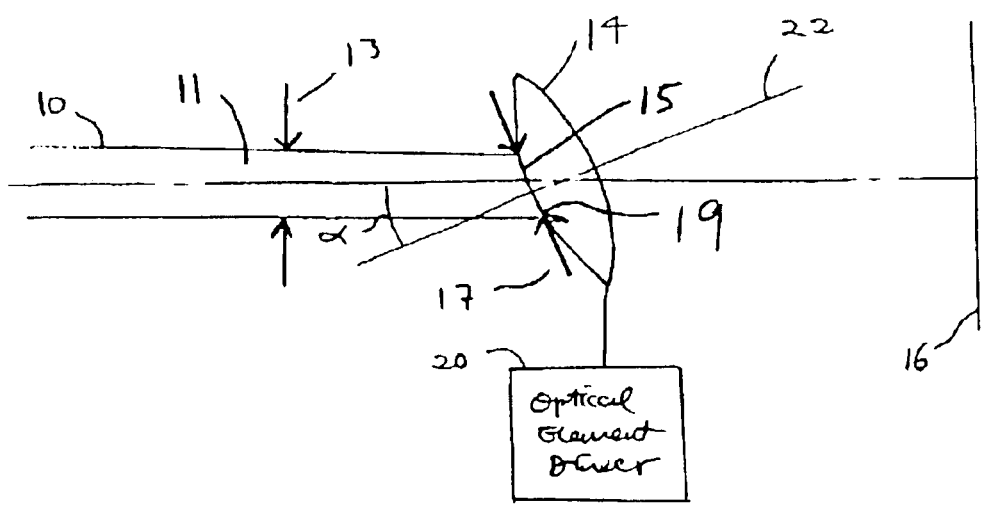
FIG. 1B is a simplified schematic diagram of a light beam passing at an angle through a lens with imperfections which is manipulated to reduce the effects of the imperfections of the lens on the light beam by moving the location of the imperfections with respect to the light beam path, in accordance with another embodiment of the present invention.

As an example of an alternative embodiment, FIG. 1B shows a setup similar to that of FIG. 1A, but the light beam 10 is disposed at an angle α with respect to the optical axis 22 of the lens 14. The lens 14 can be rotated around the optical axis 22 to change the positions of the imperfections in a manner similar to that described above in connection with the setup in FIG. 1A. If an optical element such as the lens 14 has axial symmetry around its optical axis 22, then rotation of the optical element around this axis of symmetry as described above will not substantially change the path 11 of a light beam 10 which traverses the optical element. This is true even if the light beam has no symmetry, is not parallel (i.e. is oblique) to the optical axis of the optical element, and never even intersects the optical axis (i.e. is eccentric to the optical axis). A peripheral intersecting point 19 is located near the periphery of the intersection of the path 11 of light beam 10 with the lens 14. The peripheral intersecting point 19 rotates about the optical axis 22. The peripheral intersecting point 19 is displaced by a radial distance from the optical axis, and the point travels in an approximately circular or elliptical trajectory having a circumference and a diameter. A range of motion of the lens encompasses a dimension across a trajectory of a peripheral intersecting point 19 as the lens 14 rotates about the optical axis 22. Preferably, a range of motion of the lens 14 is controlled so that the range of motion of the lens 14 is less than about twice a width 13 of the beam 10 as it intersects the lens 14. More preferably, the range of motion of the lens 14 is controlled to be about a dimension 17 across the intersecting surface area 15.

Figure 2:
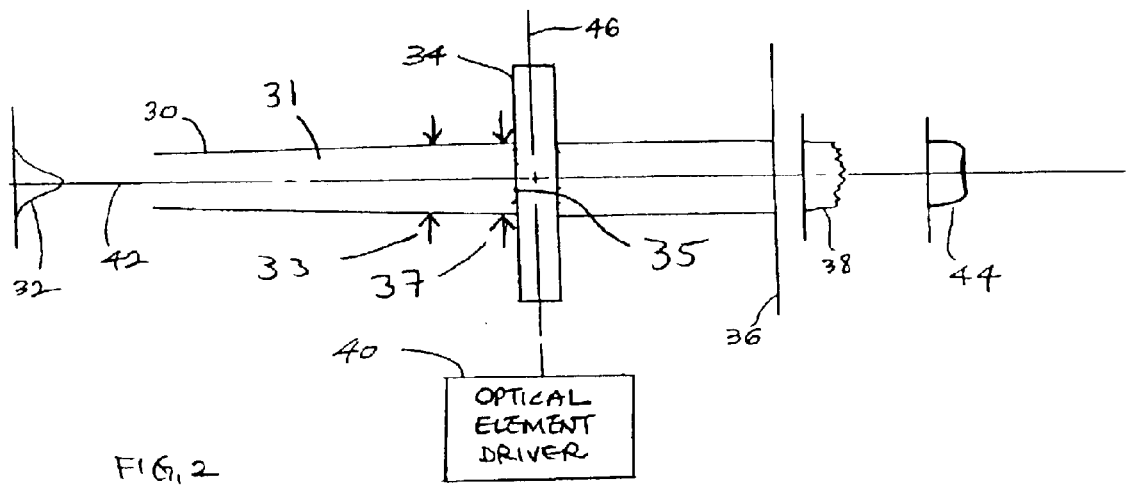
FIG. 2 is a simplified schematic diagram of a light beam passing through a diffractive optical element with imperfections which is manipulated to reduce the effects of the imperfections of the element on the light beam by moving the location of the imperfections with respect to the light beam path, in accordance with an embodiment of the present invention.

FIG. 2 shows a light beam 30 traveling along a path 31 and having an initial short axis beam energy intensity profile 32. The light beam 30 is directed through a diffractive optical element 34 and travels along the path 31 onto an illumination surface 36. The diffractive optical 34 has a diffractive grating pattern (formed by spaced etched regions such as lines, spots, or the like) on a transparent medium that is configured to transform a non-uniform beam to a spatially integrated beam with a spatial intensity distribution that is substantially uniform across the cross-section of the beam. The non-uniform beam may be an excimer laser beam having a Gaussian distribution profile 32 in the short axis. For ophthalmological surgery such as corneal ablation, the spatial intensity distribution advantageously has a top-hat shape with a circular central region that is substantially uniform and covers a large portion of the cross-section of the beam (see beam profile 44). Of course, other spatial intensity distributions are possible using different diffractive gratings.

The diffractive optic 34 has imperfections that may have been formed during manufacturing of the optical material, or may be caused by artifacts on the surfaces thereof, or may be caused by interaction of the laser beam with the optical material of the diffractive optic 34. The imperfections of the diffractive optical element 34 which are in the path of the light beam 30 produce distortions of the light beam 30 as it passes through the diffractive optic 34, as illustrated in the beam intensity profile 38 at the illumination surface 36. The profile 38 has jagged portions caused by the imperfections.

To reduce the effects of the imperfections of the diffractive optical element 34, an optical element driver 40 is provided to move the diffractive optic 14 with respect to the light beam 30 so as to change the positions of the imperfections in the path of the light beam 30. The light beam 30 has a width 33 as it intersects the diffractive optic 34. The intersection of the beam 30 with the diffractive optic 34 forms an intersecting surface 35 having a dimension 37 across the intersecting surface. As shown in FIG. 2, the diffractive optical element 34 has axial symmetry with respect to the axis 42 (although the diffractive pattern generally would not have axial symmetry), and the path of the light beam 30 is parallel to the axis 42 of the diffractive optic 34. In the specific embodiment, the path of the light beam 30 coincides with the axis 42 of the diffractive optic 34. The optical element driver 40 may be configured to rotate the diffractive optic 34 around the axis 42 so that the imperfections of the diffractive optic 34 are moved to various locations in the cross-section of the path 31 of the beam 30 over time. The rotation of the diffractive optic 34 does not substantially change the path 31 of the beam 30, and the path 31 of the light beam 30 is stable with respect to rotational motion of the diffractive optic as described above. As the beam 30 is projected to the illumination surface 36 for a period of time, the distortion is distributed over different portions of the beam 30 at the illumination surface 36. This reduces or distributes the variation, caused by the imperfections of the diffractive optic 34, in the total energy from the beam incident on any point on the illumination surface 36. The improvement by distributing the distortion is illustrated in the beam intensity profile 44, which is smoother than the profile 38. Preferably, a range of motion of the diffractive optic 34 is controlled so that the range of motion of the element is less than about twice a width 33 of the beam 30 as it intersects the diffractive optic. More preferably, the range of motion of the diffractive optic 34 is controlled to be about a dimension 37 across the intersecting surface area 35. As discussed above, the light beam 30 generally need not be parallel to or coincide with the axis 42, but may form an angle with the axis 42 (see FIG. 1B).

In another embodiment, the optical element driver 40 may be configured to move the diffractive optical element 34 in a plane 46 to distribute the distortion caused by the imperfections of the diffractive optic 34. The light beam 30 has a width 33 as it intersects the diffractive optic 34. The intersection of the beam 30 with the diffractive optic 34 forms an intersecting surface 35 having a dimension 37 across the intersecting surface. The diffractive optic 34 has geometric uniformity relative to the plane 46 (although the diffractive pattern generally would not have geometric uniformity), so that movement of the diffractive optic 34 along the plane 46 does not substantially change the path 31 of the light beam 30. In this embodiment, a substantial change to the path of the beam encompasses a change in the position of the beam path that is greater than about 10% of the width of the beam on the illumination surface. In the embodiment shown, the diffractive optic 34 is a planar optic disposed along the plane 46. The diffractive optic 34 may be moved in translation, rotation, or both translation and rotation along the plane 46 without substantially changing the path 31 of the light beam 30. In other words, the path 31 of the light beam 30 is stable with respect to motion of the diffractive optic. Preferably, a range of motion of the diffractive optic 34 is controlled so that the range of motion of the element is less than about twice a width 33 of the beam 30 as it intersects the diffractive optic. More preferably, the range of motion of the diffractive optic 34 is controlled to be about a dimension 37 across the intersecting surface area 35. Still more preferably, the range of motion of the diffractive optic 34 is controlled to be less than about 50% of a dimension 37 across the intersecting surface area 35.

Figure 3:
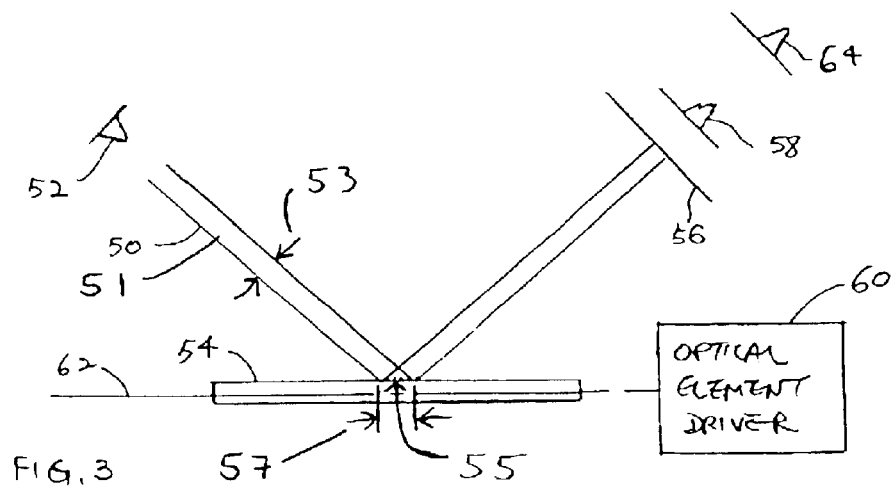
FIG. 3 is a simplified schematic diagram of a light beam reflecting from a mirror with imperfections which is manipulated to reduce the effects of the imperfections of the mirror on the light beam by moving the location of the imperfections with respect to the light beam path, in accordance with an embodiment of the present invention.

In FIG. 3, a light beam 50 having an initial beam intensity profile 52 is directed to a mirror 54 and reflected thereby onto an illumination surface 56. The beam 50 travels along a path 51. The light beam 50 has a width 53 as it reflects from the mirror 54. The intersection of the reflecting beam 50 with the mirror 54 forms an intersecting surface 55 having a dimension 57 across the intersecting surface 55. The mirror 54 has imperfections that may have been formed during manufacturing, or may be caused by particles or artifacts on the mirror surface, or may be caused by interaction of the laser beam with the optical material of the mirror 54. The imperfections of the mirror 54 which are in the path of the light beam 50 produce distortions of the light beam 50 as it is reflected by the mirror 54, as illustrated in the beam intensity profile 58 at the illumination surface 56. The profile 58 has jagged portions caused by the imperfections.

To reduce the effects of the imperfections of the mirror 54, an optical element driver 60 is provided to move the mirror 54 with respect to the path 51 of light beam 50 so as to change the positions of the imperfections in the path 51 of the light beam 50. As shown in FIG. 3, the mirror 54 has geometric uniformity relative to a plane 62, so that movement of the mirror 54 along the plane 62 does not in itself substantially change the path 51 of the light beam 50. In the embodiment shown, the mirror 54 is a planar mirror disposed along the plane 62. The mirror 54 may be moved in translation, rotation, or both translation and rotation along the plane 62 without substantially changing the path 51 of the light beam 50 by such movement. In other words, the path of the light beam 51 is stable with respect to motion of the mirror 54. In this embodiment, a substantial change to the path 51 of the beam 50 encompasses a change to the path that is greater than about 10% of the change that would occur if the mirror 54 were moved perpendicular to the plane 62. The optical element driver 60 is configured to move the mirror 54 along the plane 62 so that the imperfections of the mirror 54 are moved to various locations in the cross-section of the path 51 of the beam 50 over time. As the beam 50 is projected to the illumination surface 56 for a period of time, the distortion is distributed over different portions of the beam 50 at the illumination surface 56. This distributing reduces the variation, caused by the imperfections of the mirror 54, in the total energy from the beam incident on any point on the image plane 56. The smoothing of the distortion of the beam by distributing the distortion is illustrated in the temporally averaged beam intensity profile 64, which is smoother than the profile 58. Preferably, a range of motion of the mirror 54 is controlled so that the range of motion of the mirror 54 is less than about twice a width 53 of the beam 10 as it intersects the mirror 54. More preferably, the range of motion of the mirror 54 is controlled to be about a dimension 57 across the intersecting surface area 55. Still more preferably, the range of motion of the mirror 54 is controlled to be less than about 50% of a dimension 57 across the intersecting surface area 55.

In the embodiments shown in FIGS. 1–3, any suitable optical element driver can be used to move the lens 14, diffractive optical member 34, and mirror 54 in translation and/or rotation.

In addition to planar optics such as planar mirrors, planar diffusers, and planar diffractive optics, different optical elements may be used. For instance, other embodiments of the present invention may employ optics which have translational or linear symmetry in a plane, such as cylindrical lenses and mirrors, and linear diffractive optics (e.g., diffractive gratings). For optics having geometrical uniformity relative to a plane and a line of symmetry in that plane, a driver for moving them may oscillate the optical element back and forth along the line of symmetry or move them slowly in one direction along the line of symmetry and then return it and repeating the motion. The distortion in the light beam is distributed by moving the optical element in the plane of symmetry along the line of symmetry.

Figure 3A:
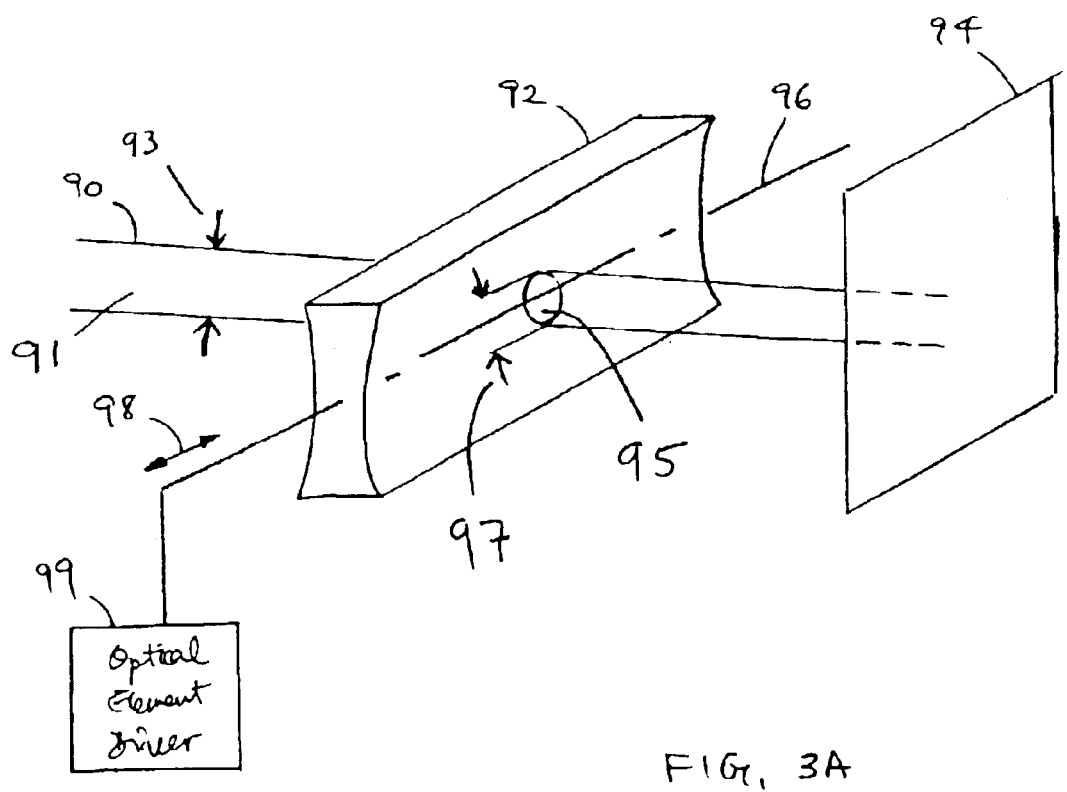
FIG. 3A is a simplified schematic diagram of a light beam passing through a cylindrical lens with imperfections which is manipulated to reduce the effects of the imperfections on the light beam in accordance with an embodiment of the present invention.

FIG. 3A shows an example of an optical system employing a cylindrical optical element. A light beam 90 is directed through a cylindrical lens 92 onto an illumination surface 94. The beam 90 travels along a path 91. The light beam 50 has a width 93 as it intersects the lens 92. The intersection of the beam 90 with the lens 92 forms an intersecting surface 95 having a dimension 97 across the intersecting surface 95. The cylindrical lens 92 has geometric uniformity relative a line of symmetry 96 in a plane. The distortion of the light beam 90 is distributed by moving the cylindrical lens 92 along the line of symmetry 96 as indicated by arrows 98 using an optical element driver 99. Moving the lens 92 along to the line of symmetry 96 moves a position of the imperfection of the lens relative to the path 91 of the laser beam without substantially changing the path of the laser beam, and the path of the laser beam 91 projected through the lens is stable as the lens 92 moves. In this embodiment, a substantial change to the path 91 of the beam 90 encompasses a change to the path that is greater than about 10% of the change that would occur if the lens 92 were moved transverse to the path 91 of the beam and perpendicular to the line of symmetry 96. Preferably, a range of motion of the lens 92 is controlled so that the range of motion of the lens 92 is less than about twice a width 93 of the beam 90 as it intersects the lens 92. More preferably, the range of motion of the lens 92 is controlled to be about a dimension 97 across the intersecting surface area 95. Still more preferably, the range of motion of the lens 92 is controlled to be less than about 50% of a dimension 57 across the intersecting surface area 95. An alternative embodiment uses a cylindrical mirror 92A driven along a line of symmetry 98A as shown in FIG. 3B.

Figure 4:
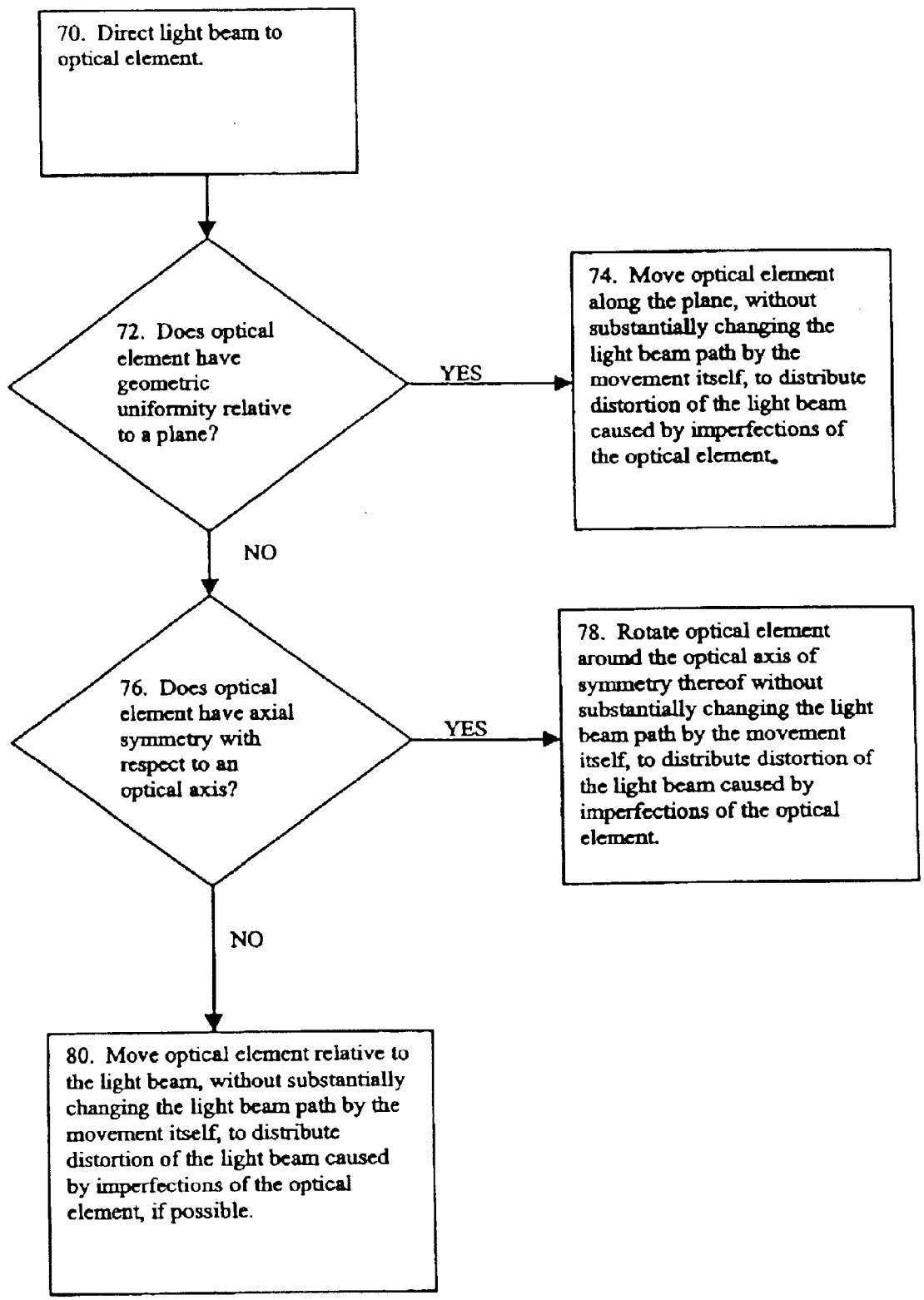
FIG. 4 is a simplified flowchart illustrating the method of reducing the effect of the variation in the beam intensity of a light beam caused by imperfections of the optical element to which the light beam is directed according to an embodiment of the invention.

FIG. 4 shows a flowchart which summarizes the method according to an embodiment of the present invention. In step 70, a light beam is directed to the optical element. A determination is made as to whether the optical element has geometric uniformity relative to a plane (step 72). If so, the optical element is moved along the plane, without substantially changing the path of the light beam by the movement in itself, to distribute the distortion of the light beam caused by imperfections of the optical element in step 74. For an optical element with a line of symmetry in the plane (e.g., the cylindrical lens 92 in FIG. 3A), the optical element is moved along the line of symmetry in the plane. For a planar optical element (e.g., the planar diffractive optical member 34 in FIG. 2 or the planar mirror 62 in FIG. 3), the planar optical element may be moved in translation and/or rotation along the plane. If there is no geometric uniformity relative to a plane, a determination is made as to whether the optical element has axial symmetry with respect to its optical axis (step 76). If so, the optical element is rotated around its optical axis to distribute the distortion of the light beam caused by imperfections of the optical element in step 78. The rotation of the optical element around its optical axis is arranged so that the rotation does not substantially change the path of the beam, and, the beam path is stable during the rotation of the optical element. Otherwise, in step 80 the optical element is moved relative to the light beam, without substantially changing the path of the light beam by the movement in itself, to distribute the distortion of the light beam caused by imperfections of the optical, provided that such a stable movement is possible.

Application in Ophthalmological Laser Surgery

Figure 5:
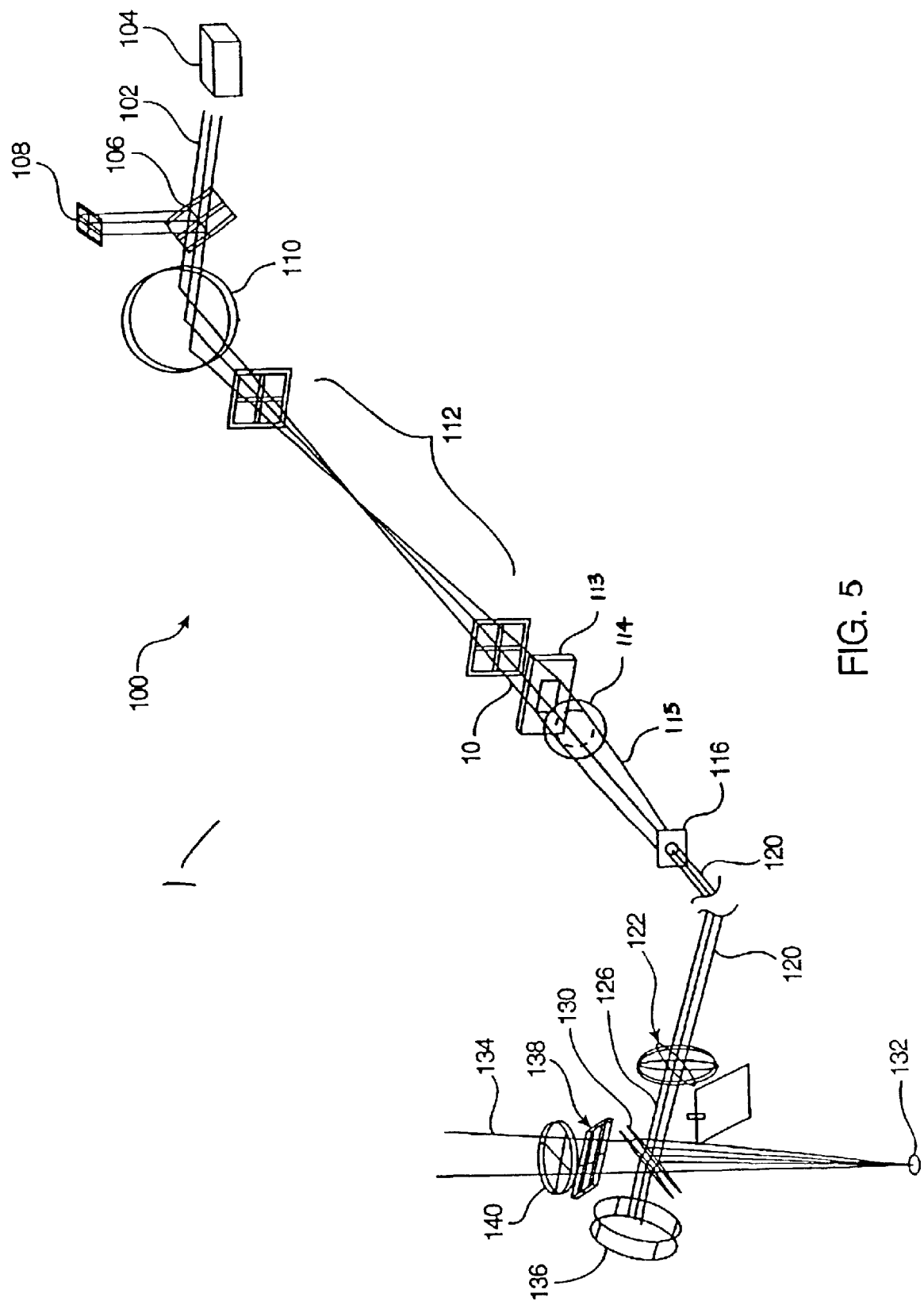
FIG. 5 is a perspective view schematically illustrating an embodiment of a laser beam optical delivery system according to an embodiment of the invention.

A preferred embodiment shown in FIG. 5 illustrates the application of the invention to an ophthalmological laser surgery system 1 comprising an optical system 100 and the relative orientation of the components in the optical system 100. By distributing the effects of the imperfections in the optical element or optical system, improved quality of surface ablation can be achieved with the laser surgery optical system 100 to provide more accurate corneal reshaping. The particular components and configurations described below are merely for illustrative purposes. The beam integration scheme or distortion distribution scheme of the present invention can be applied to a variety of different excimer laser systems.

As seen in FIG. 5, a beam 102 is generated from a suitable laser source 104, such as an argon fluoride (ArF) excimer laser beam source for generating a laser beam in the far ultraviolet range with a wavelength of about 193 nm. The wavelength typically ranges from about 192.5 to about 194 nm. In an alternate embodiment, the laser beam source employs a solid state laser source having a wavelength between 193 and 215 nm as described in U.S. Pat. No. 5,520,679 to Lin, the full disclosure of which is incorporated herein by reference. The laser beam 102 is directed to a beam splitter 106. A portion of the beam 102 is reflected onto an energy detector 108, while the remaining portion is transmitted through the beam splitter 106. The reflective beam splitter 106 may comprise a transmitting plate of partially absorbing material to attenuate the laser beam. The transmitted laser beam 102 is reflected by an adjustable mirror 110 that is used to align the path of the laser beam. In alternate embodiments, a direction of the laser beam path may be controlled with adjustable prisms. The laser beam 102 reflects from the mirror 110 onto a rotating temporal beam integrator 112 that rotates a path of the laser beam. Another type of temporal beam integrator may be used to rotate the beam. The rotated beam emerging from the temporal integrator 112 is directed to a diffractive optic apparatus including a diffractive optic 113. In a preferred embodiment, the diffractive optic 113 is rotated with the beam 102. The diffractive optic is designed so that rotation of the diffractive optic 113 does not substantially change the path of the laser beam, and the path of the laser beam is stable with respect to rotation of the diffractive optic. The beam passes through the diffractive optic 113 and positive lens 114 and emerges as a converging beam 115. The converging beam 115 travels to the spatial integration plane at which a variable aperture 116 is disposed. The spatial integration plane is disposed near the focal point of the positive lens 114. An apertured beam 120 emerges from the variable aperture 116. The variable aperture 116 is desirably a variable diameter iris combined with a variable width slit (not shown) used to tailor the size and profile of the beam 115 to a particular ophthalmological surgery procedure, such as photorefractive keratectomy (PRK) and phototherapeutic keratectomy (PTK).

Figure 6:
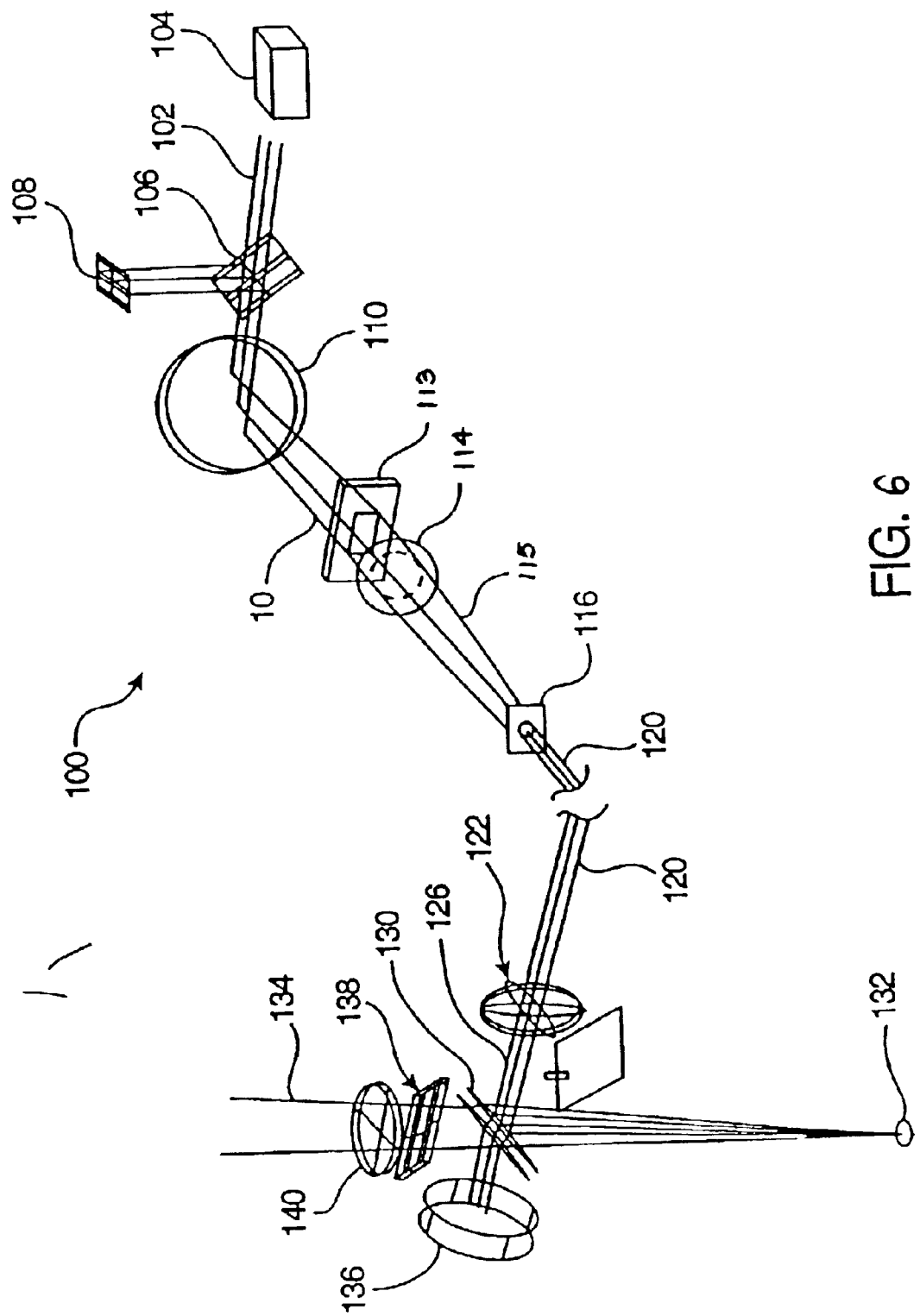
FIG. 6 is a perspective view schematically illustrating an embodiment of a laser beam optical delivery system according to another embodiment of the invention.

The apertured beam 120 is directed onto an imaging lens 122, which may be a biconvex singlet lens with a focal length of about 125 mm. The beam 126 emerging from the imaging lens 122 is reflected by a mirror/beam splitter 130 onto the surgical plane 132. The apex of the cornea of the patient is typically positioned at the surgical plane 132. Imaging lens 122 may be moved transverse to the beam to offset the imaged beam in order to scan the imaged beam about the surgical treatment plane 132. A treatment energy detector 136 senses the transmitted portion of the beam energy at the mirror/beam splitter 130. A beam splitter 138 and a microscope objective lens 140 form part of the observation optics. If desired, a beam splitter may be installed in the optical path 134 of the microscope objective lens. The beam splitter is optically coupled to a video camera to assist in viewing or recording the surgical procedure. Similarly, a heads-up display may also be inserted in the optical path of the microscope objective lens 140 to provide an additional observational capability. Other ancillary components of the laser optical system 100 which are not necessary to an understanding of the invention such as the movable mechanical components driven by an astigmatism motor and an astigmatism angle motor, have been omitted to avoid prolixity. An alternate embodiment shown in FIG. 6 illustrates an embodiment of the optical system 100 without the rotating temporal beam integrator 112 of FIG. 5. In another embodiment of the optical system 100, the diffractive optic 113 is replaced with an array of rotating prisms attached to the integrator 112 as described in U.S. Pat. Nos. 5,646,791 and 5,912,775, issued to Glockler.

A number of the optical elements in the optical system 100 may be moved as described above to distribute the distortion caused by imperfections of the optical elements. In a preferred embodiment, the lens 114 is rotated around its axis. In other embodiments, the beam splitter 106 may be moved along its plane; the mirror 110 may be moved along its plane; the diffractive optic 113 may be moved in its plane, and the mirror/beam splitter 130 may be moved along its plane. Although the path of the light beam is stable with respect to movement of an optical element as described above, other elements of the optical system 100 may change the path of the light beam as it travels through the optic.

The ophthalmological laser surgery optical system 1 preferably employs the ultraviolet laser beam in corneal ablation procedures to ablate corneal tissue in a photodecomposition that does not cause thermal damage to adjacent and underlying tissue. Molecules at the irradiated surface are broken into smaller volatile fragments without substantially heating the remaining substrate; the mechanism of the ablation is photochemical, i.e. the direct breaking of intermolecular bonds. The ablation removes a layer of the stroma to change its contour for various purposes, such as correcting myopia, hyperopia, and astigmatism. Such systems and methods are disclosed in the following U.S. patents, the disclosures of which are hereby incorporated by reference in their entireties for all purposes: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. Pat. No. 5,163,934 issued Nov. 17, 1992 for "PHOTOREFRACTIVE KERATECTOMY"; and U.S. Pat. No. 5,556,395 issued Sep. 17, 1996 for "METHOD AND SYSTEM FOR LASER TREATMENT OF REFRACTIVE ERROR USING AN OFFSET IMAGE OF A ROTATABLE MASK."

Figure 7:
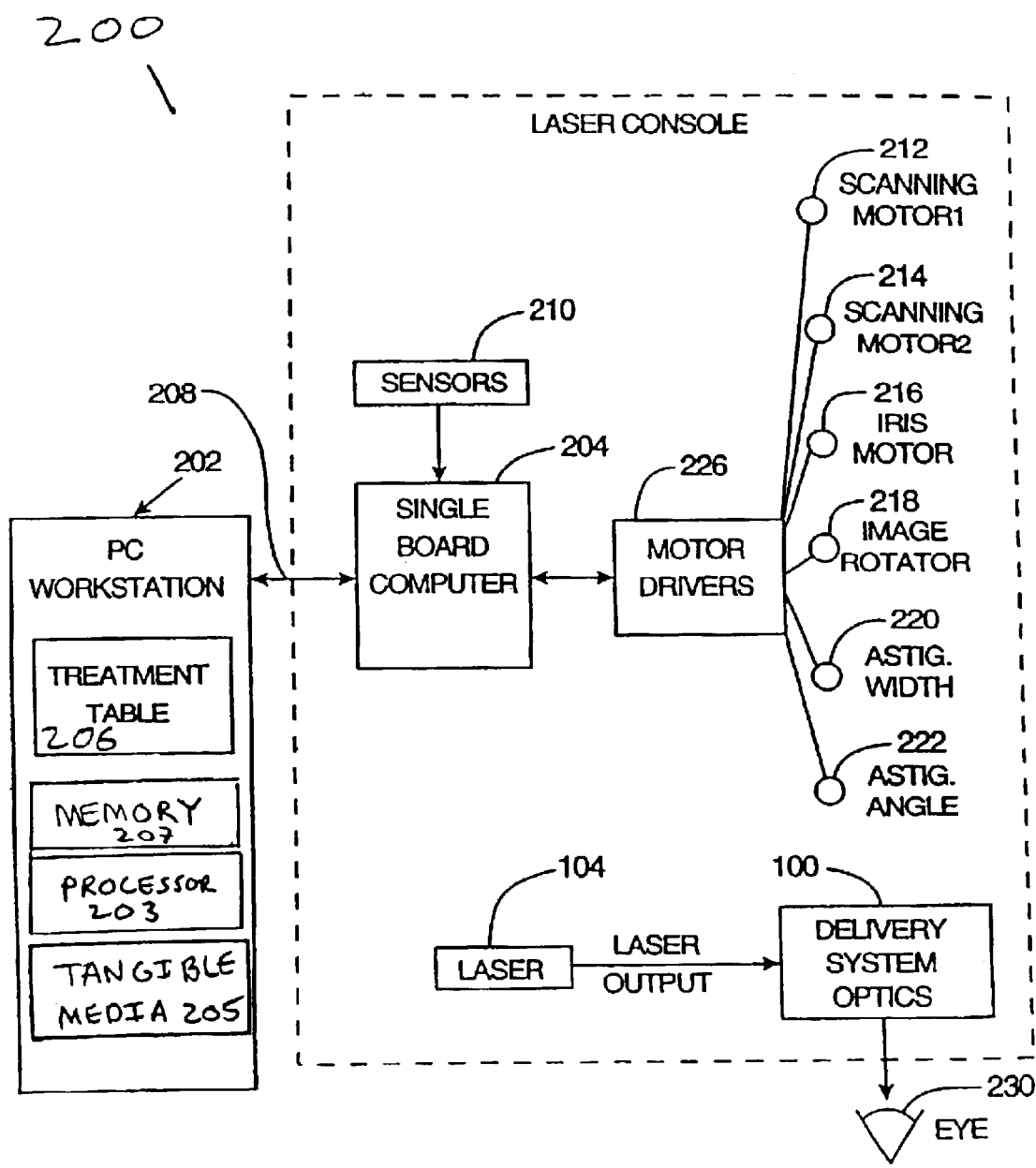
FIG. 7 is a block diagram of a control system used in an ophthalmological surgery system according to an embodiment of the invention.
Figure 8:
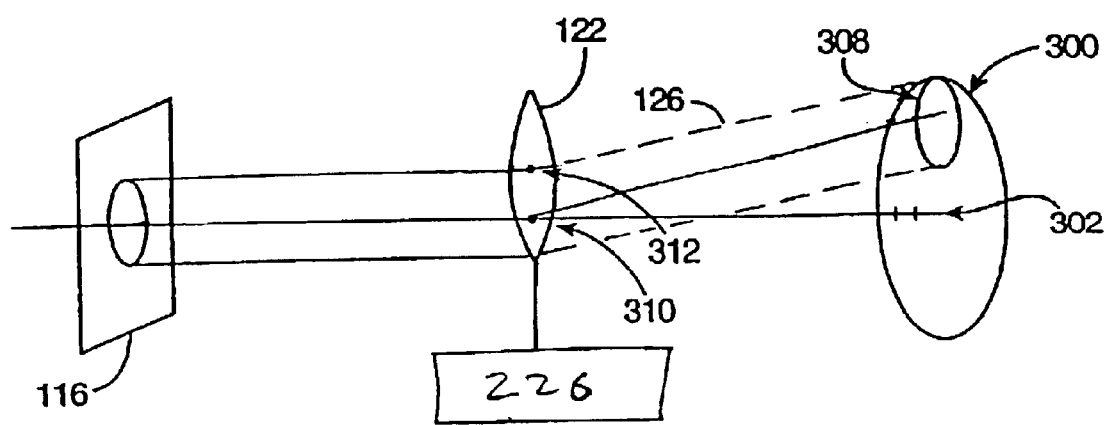
FIG. 8 is a plan view illustrating a scanning embodiment of the invention.

The block diagram of FIG. 7 illustrates a control system 200 of an ophthalmological surgery system 1 for incorporating the invention. The control system includes a personal computer (PC) work station 202 coupled to a single board computer 204 of the laser surgery system 200 by means of a first bus connection 208. The PC workstation 202 comprises a processor 203, a memory 207 and a tangible media 205 that includes instructions readable by processor 203. The PC work station 202 and the subcomponents of the laser surgery system 1 and control system 200 are known components and may comprise the elements of the VISX TWENTY/TWENTY™ EXCIMER LASER SYSTEM or the VISX STAR™, STARS2™, or STARS3™ Excimer Laser System, which are available from VISX, Incorporated of Santa Clara, Calif. The laser surgery system 200 includes a plurality of sensors generally designated with reference numeral 210 which produce feedback signals from the movable mechanical and optical components in the ophthalmological laser surgery optical system 100 of FIG. 5 or FIG. 6. The movable mechanical and optical components include, for example, the elements driven by an iris motor 216, an image rotator 218, and astigmatism width motor 220, and an astigmatism angle motor 222. For scanning treatments where an ablation from an individual laser pulse is variably offset from the treatment center, scanning motor 1 (212) and scanning motor 2 (214) are provided. In FIG. 8, moving the lens 122 transverse to the beam 120 will provide this variable offset. The feedback signals from the sensors 210 are provided via appropriate signal conductors to the single board computer 204, which is desirably an STD bus compatible single board computer using a type 8031 microprocessor. The single board computer 204 controls the operation of the motor drivers generally designated with reference numerals 226 for operating the elements 216, 218, 220, and 222. In addition, the single board computer 204 controls the operation of the excimer laser 104, which is desirably an ArF laser with a 193 nanometer wavelength output designed to provide feedback stabilized fluence of 160 millijoules per cm at the cornea of the patient's eye 230 via the optical system 100 of FIG. 5 or FIG. 6. Other ancillary components of the laser surgery system 1 which are not necessary to an understanding of the invention, such as a high resolution microscope, a video monitor for the microscope, a patient eye retention system, and an ablation effluent evacuator/filter, as well as the gas delivery system, have been omitted to avoid prolixity. Similarly, the keyboard, display, and conventional PC subsystem components, such as flexible and hard disk drives, memory boards and the like, have been omitted from the depiction of the PC work station 202.

The laser surgery system 1 may be used for procedures such as photorefractive keratectomy (PRK) and phototherapeutic keratectomy (PTK). Using PC workstation 202, an operator enters at least one patient treatment parameter such as the desired change in patient refraction. The above treatment parameter corresponds to an improved change corneal shape. The PC workstation 202 may then calculate treatment table 260 containing the positions of the optical elements during laser treatment. The optical elements are typically varied during treatment include variable aperture 116 and the position of the lens 122. In PRK, for instance, the laser surgery system 200 is used to ablate the tissue of the cornea after removal of the epithelium. To correct for myopia, the circular laser beam 115 is adjusted to a circular spot registered with the treatment area on the cornea using the adjustable aperture 116. The circular spot varies typically between a 0.5 mm circle and a 6 mm circle. The correction for myopia reduces the radius of curvature of the cornea. This requires removal of more tissue in the center of the cornea and less tissue toward the peripheral treatment area. A first pulse of the apertured beam 120 can ablate away tissue from the entire treatment area, but successive pulses are reduced in diameter by the variable aperture 116 so that the pulses become successively smaller. In another embodiment, successive pulses are incrementally increased from a small to large diameter covering the treatment area. This removes more tissue from the central region and brings the cornea to the desired contour having a decreased curvature. After the photorefractive keratectomy procedure, the epithelium rapidly regenerates over the shaped area, producing a new anterior surface of the cornea. Alternatively, the epithelium is not removed but is partially severed and moved to the side for surgery and returned to its original position after the PRK (LASIK procedure).

In a preferred embodiment the laser surgery system 1 scans the laser beam over a treatment area as shown in FIG. 8. The treatment area 300 of the cornea comprises a plurality of smaller areas ablated with individual laser pulses, such as the offset imaged apertured beam 126. The positions and sizes of the smaller ablated areas correspond to the values calculated in the treatment table 260. The decrease in curvature to correct myopia is accomplished by the scanning beam 126 about the cornea. As shown in FIG. 8, the offset position 312 of the lens 122 is varied about the central position 310 by appropriate motor drivers 226. This scanning produces an offset imaged apertured beam 126 with an outer portion 308. The beam 126 preferably cover the center 302 of the treatment area 300 during a portion of the scanning treatment for myopia. Optionally, a dimension of the variable aperture 116 may be varied during scanning to vary the size and shape of the beam 126. The successive pulses of the scanning beam contour the desired decreased curvature according to the treatment table 260.

For correcting hyperopia, the apertured beam 120 of FIG. 5 or FIG. 6 scans over a treatment area of the cornea. As shown in FIG. 8, the treatment area 300 of the cornea comprises a plurality of smaller areas ablated with individual laser pulses, such as the offset imaged apertured beam 126. The positions and sizes of the smaller ablated areas correspond to the values calculated in the treatment table 260. More tissue must be removed from the periphery of the treatment area than from the center. This tissue removal pattern increases the radius of curvature of the cornea. The increase in curvature is accomplished by scanning the beam 126 about the cornea. As shown in FIG. 8, the offset position 312 of the lens 122 is varied about the central position 310. This scanning produces an offset images apertured beam 126 with an outer portion 308. Desirably, the beam 126 does not cover the center 302 of the treatment area 300 during any portion of the scanning treatment. Optionally, a dimension of variable aperture 116 may be varied during scanning to vary the size and shape of the beam 126. Successive pulses of the scanning beam contour the cornea to the desired increased curvature according to the treatment table 260.

For correcting astigmatic properties of the cornea, the variable width slit (not shown) diametrically spans the treatment area of the cornea which is generally rectangular. The first pulse of the imaged apertured beam 126 ablates a generally rectangular area of corneal tissue. Successive pulses are directed with varying width of the generally rectangular spot of the imaged apertured beam 126 which are symmetrically positioned with respect to the optical center. The astigmatism correcting change is effected by volumetric removal of the corneal tissue.

The distortion distribution scheme of the present invention may be applied to different laser systems, including scanning lasers and large area laser ablation systems. Examples include the VISX STAR™, STAR S2™, STAR S3™ Excimer Laser Systems, which are commercially available from VISX, Incorporated of Santa Clara, Calif. Other laser systems include the T-PRKR scanning and tracking laser from Alcon Summit (which acquired the original manufacturer Autonomous Technologies Corporation), the SVS Apex laser from Alcon Summit, the Keracor™ 117 and Technolas® 217A from Bausch & Lomb (which acquired the original manufacturers, Chiron Vision and Technolas), the LaserSight Laserscan LSX scanning laser from LaserSight, Incorporated, the Meditec MEL-70 from Aesculap-Meditec, the Allegretto Wave from Wavelight Technologies, and the like.

The distortion distribution scheme is simple and inexpensive, and does not require any reconfiguration of the optical elements. Any suitable optical element drivers may be used to move the optical elements in translation and/or rotation. The optical element drivers are easy to use and maintain.

While the above provides a full and complete disclosure of the preferred embodiments of the invention, various modifications, alternate constructions and equivalents may be employed as desired. Although specific examples given above involve axial symmetry of the optical element with respect to the optical axis or geometric uniformity of the optical element relative to a plane, the invention can be applied in other cases where movement of the optical element to change positions of the imperfections of the optical element relative to the path of the light beam does not in itself substantially change the path of the light beam. In those cases, the movement may require more elaborate control to stabilize the path of the light beam. Also, although specific reference has been made to ablating corneal tissue with an excimer laser, any suitable pulsed laser such as a pulsed infrared or pulsed ultraviolet laser may be used. Therefore, the above description and illustrations should not be construed as limiting the invention, which is defined by the appended claims.

What is claimed is:

1. A method of temporally smoothing a distortion of a light beam intensity distribution, the method comprising:
   directing the light beam to an optical system, the optical system comprising an optical element disposed along a light beam path, the optical element having an imperfection in a path of the light beam causing the distortion of an energy profile distribution of the light beam; and
   moving the optical element with respect to the light beam path to change a position of the imperfection in the path of the light beam, the moving of the element distributing the distortion caused by the imperfection.

2. The method of claim 1 wherein the path of the light beam is stable with respect to the moving optical element.

3. The method of claim 2 further comprising controlling a range of motion of the element during the step of moving, the range of motion being less than about twice a width of the beam intersecting the element.

4. The method of claim 3 wherein the optical element is axially symmetric with respect to an optical axis of the optical element, and wherein the distortion of the light beam is temporally distributed by rotating the optical element around the optical axis of symmetry thereof.

5. The method of claim 4 wherein the path of the light beam is parallel to the axis of symmetry of the optical element.

6. The method of claim 5 wherein the path of the light beam coincides with the axis of symmetry of the optical element.

7. The method of claim 4 wherein the path of the light beam is oblique to and eccentric with the optical axis of the optical element.

8. The method of claim 3 wherein the optical element is selected from the group consisting of a lens, a mirror, a beam splitter, a transmitting plate, a prism and a diffractive optic.

9. The method of claim 3 wherein the optical element has geometric uniformity relative to a plane, and wherein the distortion of the light beam is distributed by moving the optical element along the plane.

10. The method of claim 9 wherein the optical element is moved by translation in at least one direction along the plane.

11. The method of claim 9 wherein the planar optical element is moved by rotation around an axis.

12. The method of claim 9 wherein the optical element is a planar optical element.

13. The method of claim 12 wherein the optical element is selected from the group consisting of a planar mirror, a planar beam splitter, and a planar diffractive optic.

14. The method of claim 3 wherein the optical element is selected from the group consisting of a cylindrical lens, a cylindrical mirror, and a diffractive optical element with linear symmetry.

15. The method of claim 3 wherein the light beam intersects the optical element over an intersecting surface of the element, the intersecting surface having an intersection area and a dimension across the area, and wherein the range of motion of optical element is less than about 50% of the dimension across the intersection area.

16. The method of claim 3 wherein the light beam is a pulsed laser beam.

17. The method of claim 3 wherein the optical element has geometric uniformity relative a line of symmetry in a plane, and wherein the distortion of the light beam is distributed by moving the optical element along the line of symmetry in the plane.

18. The method of claim 17 wherein the optical element is selected from the group consisting of cylindrically symmetric optical elements and linearly symmetric optical elements.

19. A system for temporally smoothing an energy intensity distribution of a light beam, the system comprising:
   a light source for making a the beam of light energy;
   an optical element disposed in a path of the light beam, the optical element having an imperfection in the path of the light beam causing a distortion of the energy intensity distribution of the light beam; and
   an optical element driver coupled with the optical element to move the optical element with respect to the light beam path to change a position of the imperfection in the path of the light beam, the changed position distributing the distortion of the light beam caused by the imperfection of the optical element.

20. The system of claim 19 wherein the path of the light beam is stable with respect to the optical element changing the position of the imperfection.

21. The system of claim 20 wherein the driver controls a range of motion of the optical element, the range of motion being less than about twice a width of the beam as the beam intersects the element.

22. The system of claim 21 wherein the light source is a pulsed laser.

23. The system of claim 21 wherein the optical element has a geometric uniformity relative to a plane, and wherein the optical element driver is configured to move the optical element along the plane.

24. The system of claim 23 wherein the optical element is a planar optical element.

25. The system of claim 24 wherein the planar optical element is selected from the group consisting of a planar mirror, a planar beam splitter, a prism, a transmitting plate, and a planar diffractive optic.

26. The system of claim 23 wherein the optical element has geometric uniformity relative to a line in the plane.

27. The system of claim 26 wherein the optical element is selected from the group consisting of a cylindrical lens, a cylindrical mirror and a cylindrical diffractive optic.

28. The system of claim 21 wherein the optical element is axially symmetric with respect to an optical axis of the optical element, and wherein the optical element driver is configured to rotate the optical element around the optical axis of symmetry thereof.

29. The system of claim 28 wherein the path of the light beam is parallel to the optical axis of the optical element.

30. The system of claim 29 wherein the path of the light beam coincides with the axis of symmetry of the optical element.

31. The system of claim 28 wherein the path of the light beam is oblique to the optical axis of the optical element.

32. The system of claim 28 wherein the optical element is selected from the group consisting of a lens, a mirror, a beam splitter, a prism, a planar transmitting plate and a diffractive optical member.

33. The system of claim 21 wherein the light beam intersects the optical element over an intersecting surface of the element, the intersecting surface having an intersecting area and a dimension across the area, and wherein the range of motion of the optical element is less than about 50% of the dimension across the intersecting area.

34. A method of temporally smoothing an ablation in a material at a laser treatment plane using a pulsed laser beam, the method comprising:

making the pulsed laser beam with a pulsed laser;

directing the pulsed laser beam to an optical system comprising an optical element disposed along a laser beam path, the optical element having an imperfection in a path of the laser beam, the imperfection causing a distortion of the laser beam;

moving the optical element with respect to the path of laser beam to change a position of the imperfections in the path of the laser beam, the moving of the element distributing the distortion caused by the imperfection; and ablating the material with the laser beam to form an ablation in the material.

35. The method of claim 34 wherein the path of the laser beam is stable with respect to the moving optical element.

36. The method of claim 35, further comprising:

controlling a range of motion during the step of moving, the range of motion being less than about twice a width of the beam intersecting the element; and wherein the material ablated with the laser beam is a corneal material and the pulsed laser is an excimer laser.

37. The method of claim 36 wherein the optical element having one or more imperfections has geometric uniformity relative to a plane, and is moved along the plane to change the position of the imperfections in the path of the laser beam.

38. The method of claim 36 wherein the optical element having an imperfection has geometric uniformity along a line in a plane and is moved along the line in the plane to change a position of the imperfections in the path of the laser beam.

39. The method of claim 36 wherein the optical element is axially symmetric with respect to an optical axis of the optical element, and the optical element is rotated around the optical axis of symmetry to change the position of the imperfection in the path of the laser beam.

40. A system for forming an ablation in a material at a laser treatment plane using a pulsed laser beam, the system comprising:

a pulsed laser source for making a pulsed laser beam;

an optical system directing the laser beam toward the treatment plane and comprising an optical element disposed along a path of the laser beam, the optical element having an imperfections in the path of the laser beam causing a distortion of the laser beam; and an optical element driver coupled with the optical element to move the optical element with respect to the laser beam path to change a position of the imperfection in the path of the laser beam, the distortion of the laser beam caused by the imperfection being distributed by the changed position.

41. The system of claim 40 wherein the path of the light beam is stable with respect to the optical element driver changing the position of the imperfection.

42. The system of claim 41 wherein the driver controls a range of motion of the optical element, the range of motion being less than about twice a width of the beam as the beam intersects the element, and wherein the material ablated with the laser beam is a corneal material, and the pulsed laser is an excimer laser.

43. The system of claim 42 wherein the optical element having an imperfection has geometric uniformity relative to a plane, and wherein the optical element driver is configured to move the optical element along the plane to change a position of the imperfection in the path of the laser beam.

44. The system of claim 42 wherein the optical element having one or more imperfections has geometric uniformity along a line in a plane and is moved along the line of symmetry in the plane to change the position of the imperfection in the path of the laser beam.

45. The system of claim 42 wherein the optical element is axially symmetric with respect to an optical axis of the optical element, and wherein the optical element driver is configured to rotate the optical element around the optical axis to change the position of the imperfection in the path of the laser beam.

* * * * *